United States Patent [19]

Nakagawa et al.

[11] Patent Number: 5,409,815
[45] Date of Patent: Apr. 25, 1995

[54] DNA'S ENCODING SIGNAL PEPTIDES

[75] Inventors: Yukimitsu Nakagawa; Naofumi Hayasuke; Atsushi Masaki; Yutaka Ishida; Kohji Murakami; Ken Okabayashi; Kiyoshi Tsutsui; Hitoshi Minamino; Kazuo Ikegaya; Kaoru Kobayashi; Haruhide Kawabe, all of Osaka; Sadao Ueda, Kyoto, all of Japan

[73] Assignee: The Green Cross Corporation, Osaka, Japan

[21] Appl. No.: 311,556

[22] Filed: Feb. 16, 1989

[30] Foreign Application Priority Data

Feb. 16, 1988 [JP] Japan .................. 63-33657

[51] Int. Cl.$^6$ ..................... C12P 21/06; C07H 21/04
[52] U.S. Cl. .................... 435/69.1; 435/172.3; 435/243; 435/254.2; 435/320.1; 436/501; 536/22.1; 536/24.1; 536/24.2; 935/6; 935/8; 935/22; 935/47; 935/48; 935/66
[58] Field of Search ............ 435/6, 69.1, 172.3, 435/243, 320.1, 254.2; 436/501; 536/27, 24.1; 935/9, 19, 77, 78, 88

[56] References Cited

U.S. PATENT DOCUMENTS 4,775,622 10/1988 Hitzeman et al. .............. 435/68

FOREIGN PATENT DOCUMENTS 0127304 12/1984 European Pat. Off. .

OTHER PUBLICATIONS

Takahashi et al. (1987) Proc. Nat'l Acad Sci (USA) vol. 84, pp. 4413–4417.
Von Heijne (1985) J. Mol. Biol, vol. 184, pp. 99–105.
Von Heijne (1984) J. Mol. Biol, vol. 173, 243–251.
Perlman et al (1983) J. Mol. Biol, vol. 167, pp. 391–409.
Von Heijne, Eur. J. Biochem. 133, 17–21 (1983).
Von Heijne, Eur. J. Biochem. 103, 431–438 (1980).
Blobel et al, Journal of Cell Biology, vol. 67, 1975, 835–851.
Briggs et al., Advances in Protein Chemistry, vol. 38 1986, pp. 109–181.
Von Heijne, The EMBO Journal, vol. 3, No. 10, 2315–2318, 1984.
Bergman et al. The Journal of Biological Chemistry, vol. 254, No. 18 8869–8876 1979.
Von Heijne, Nucleic Acids Research, vol. 14, No. 11 1986 pp. 4683–4690.
Spostrom et al, The Embo Journal, vol. 6, No. 3, Mar. 1987, pp. 832–831.
Yamamoto et al, Biochemical and Biophysical Research Communications, vol. 149, No. 2, Dec. 16, 1987, pp. 431–436.
Kendall et al. Nature, vol. 321, Jun. 12, 1986, pp. 706–709.

Primary Examiner—Margaret Parr
Assistant Examiner—Ardin H. Marschel
Attorney, Agent, or Firm—Sughrue, Mion, Zinn, Macpeak & Seas

[57] ABSTRACT

Novel signal peptides capable of functioning in yeasts have the amino acid sequence:

Met-$A_1$-$A_2$-X-B-C-D-E-F wherein $A_1$ is a peptide chain composed of 1–3 amino acids each selected from the group consisting of Arg, Ser, Lys and His, $A_2$ is a peptide chain composed of 1–3 amino acids, X is a peptide chain composed of 8–10 hydrophobic amino acids, B is Pro or Ser, C is Gly or Pro, D Cys, Ala, Leu, Ser, Thr and Val, E is Trp or Gln and F is Ala or Gly. DNA sequences coding for these signal peptides can be used for the secretory expression of heterologous proteins in yeasts.

13 Claims, 9 Drawing Sheets

- Xba I digestion
- DNA polymerase I, Klenow fragment and dATP, dGTP, dTTP, dCTP,
- pCGGATCCG (BamHI linker) T4 DNA ligase
- BamHI digestion
- T4 DNA ligase

DNA'S ENCODING SIGNAL PEPTIDES

FIELD OF THE INVENTION

This invention relates to novel signal peptides capable of functioning in yeasts and to secretory expression of heterologous proteins using said signal peptides.

BACKGROUND OF THE INVENTION

In causing a transformant host to produce a desired protein by the recombinant DNA technology, it is advantageous in many aspects that the host is capable of secretory expression of the desired protein. Thus, in cases where a desired protein, if directly expressed in the host cell, shows toxicity which is inconvenient for the growth and survival of the host, secretory expression of the desired protein can avoid this toxicity.

In some cases, a desired protein, if accumulated in large amounts in the host cell, may inhibit the growth of the host even when the protein does not show toxicity. Secretory expression can avoid such circumstances as well.

In producing a desired protein on a commercial scale by using the recombinant DNA technology in a system in which the desired protein is accumulated intracellularly to purify the desired protein, it is necessary to disrupt the cells and purify the protein from the disruption mixture. It is difficult to obtain the desired protein in high purity by such a purification method since the product protein is contaminated by many impurities coming from the transformant host.

On the contrary, in producing a desired protein in a secretory expression system, the desired protein can be purified from the culture broth and accordingly the contamination with recombinant host-derived impurities can be minimized. This is a great merit.

Many proteins undergo modifications such as sugar chain addition, disulfide bond formation, activation by limited hydrolysis of inactive precursor proteins and phosphorylation or carboxylation of specific amino acids. These modifications are common to various cells, and among these, sugar chain addition and disulfide bond formation take place in the process of secretion.

Most of natural secreted proteins have sugar chain(s) or disulfide bond(s) intra- or intermolecularly. When the protein is produced in the host cells, disulfide bond(s) to be formed are not formed or are incorrectly formed to thereby cause degeneration and insolublization of the protein (GB Patent 0092182). Therefore, the production of a desired protein in the manner of secretory expression is expected to give the protein, having sugar chain(s) or disulfide bond(s), in a form more close in function and structure to a natural protein as compared with the system in which the protein is accumulated intracellularly.

Some findings are available concerning the properties of signal peptides which are essential for secretory protein expression. The characteristic features of their amino acid sequences are as follows. Basic amino acids are found in relatively large numbers in the vicinity of the N terminus while polar amino acids are found in relatively large numbers in the vicinity of that site on the C terminal side which is digested by signal peptidase. A sequence of hydrophobic amino acids is found in the middle. The basic amino acids in the vicinity of the N terminus are supposed to interact with phospholipids on the cell inside surface, the sequence of hydrophobic amino acids in the middle presumably plays an important role in passage through the cell membrane, and the C-terminal polar amino acids supposedly play a role of the recognition site in digestion by signal peptidase. Such characteristics are very similar in organisms from procaryotes to higher animals and suggest a common protein secretion mechanism [cf. M. S. Briggs and L. M. Gierasch (1986), Adv. Protein Chem., 38, 109–180; G. von Heijne (1984), EMBO J., 3, 2315–2318; G. von Heijne (1984), J. Mol. Biol., 173, 249–251; D. Perlman and H. O. Halvorson (1983), J. Mol. Biol., 167, 391–409].

G. von Heijne studied the amino acid sequences of signal peptides of procaryotes and eucaryotes and reported characteristic features of the amino acid sequence from the sequence of hydrophobic amino acids in the middle to the signal peptidase cleavage site on the C terminal side [G. von Heijne (1986), Nucl. Acids Res., 14, 4683–4690; G. von Heijne (1985), J. Mol. Biol., 184, 99–105; G. von Heijne (1983), Eur. J. Biochem., 133, 17–21]. According to the report, in eucaryotic cells, hydrophobic amino acids, in particular leucine, are detected frequently in the portion from $-13$ to $-6$ (the amino acid just preceding the signal peptide cleavage site being numbered $-1$). Hydrophobic amino acids such as phenylalanine, alanine, isoleucine and valine and further cysteine, methionine and the like are also detected in relatively high frequencies. As for the amino acids from $-5$ to $-1$, amino acids with relatively high polarity are found in high frequencies. The sequence constructed by amino acids showing highest detection frequencies is as follows.

| $-13$ | $-12$ | $-11$ | $-10$ | $-9$ | $-8$ | $-8$ | $-7$ | $-5$ | $-4$ |
|---|---|---|---|---|---|---|---|---|---|
| Leu | Leu | Leu | Leu | Leu | Leu | Leu | Leu | Pro | Gly |

| $-3$ | $-2$ | $-1$ | $+1$ | $+2$ |
|---|---|---|---|---|
| Cys | Trp | Ala | Gln | Pro |

The signal peptide is cleaved between $-1$ and $+1$. Therefore, the amino acids numbered $+1$ and $+2$ are the N terminus of mature proteins. Many signal peptides are generally composed of 15–30 amino acids, and a basic amino acid sequence is further required on the upstream N terminus side even for the signal sequence shown above. The basic amino acids include arginine, lysine and histidine, and these may occur either singly or in plurality.

However, when a known signal peptide is used for secretory expression of a heterologous protein, it often occurs that the resulting product is different in structure from a natural form.

SUMMARY OF THE INVENTION

In view of the above, it is an object of the invention to provide universal signal peptides enabling efficient secretory expression of the desired protein.

As a result of investigations on signal peptides constituting vectors essential for secretory expression of proteins in yeasts, the present inventors found that signal peptides having a specific structure can function as signal peptides of vectors in yeasts, and further investigations based on this finding have now led to completion of the present invention.

Thus, the invention relates to the following aspects (1) to (6):

(1) A signal peptide having the specific structure shown hereinbelow;

(2) A pre-protein comprising the signal peptide mentioned under (1) followed by a heterologous protein;
(3) A DNA sequence coding for the signal peptide mentioned under (1);
(4) A recombinant plasmid which contains a DNA sequence coding for the signal peptide mentioned under (1) and is intended for use in transforming yeasts;
(5) A yeast transformed with the recombinant plasmid containing a DNA sequence coding for the signal peptide mentioned under (1); and
(6) A method of causing secretory expression of a heterologous protein from a yeast transformed with a recombinant plasmid containing a DNA sequence coding for the signal peptide mentioned under (1).

The recombinant plasmid according to the present invention is composed of a DNA sequence coding for the signal peptide, a DNA sequence coding for a heterologous protein, a promoter, a terminator and a plasmid DNA.

The signal peptide specific in structure as mentioned above under (1) is represented by the following amino acid sequence (I):

Met-A1-A2-X-B-C-D-E-F            (I)

In the above formula, $A_1$ is a peptide chain composed of 1–3 amino acids each selected from the group consisting of Arg, Ser, Lys and His, $A_2$ is a peptide chain composed of 1–3 amino acids, X is a peptide chain composed of 8–10 hydrophobic amino acids, B is Pro or Ser, C is Gly or Pro, D is an amino acid selected from the group consisting of Cys, Ala, Leu, Ser, Thr and Val, E is Trp or Gln and F is Ala or Gly.

DETAILED DESCRIPTION OF THE INVENTION

Figure 1:
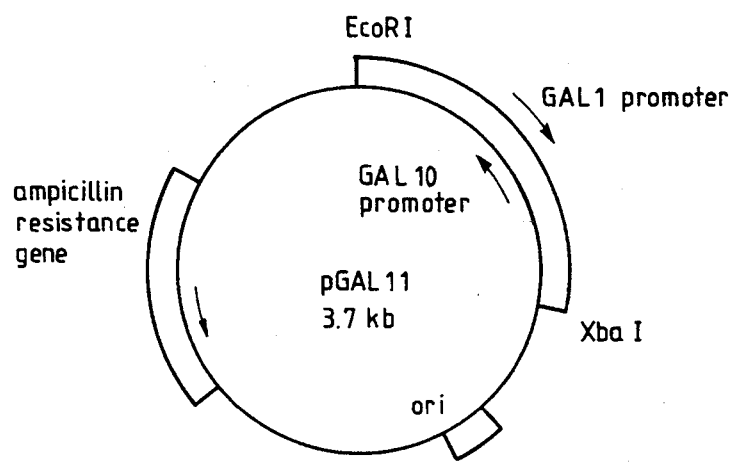
FIG. 1 shows a process for constructing a plasmid, pGAL12, from a GAL1, 10 promoter containing plasmid, pGAL11.
Figure 1:
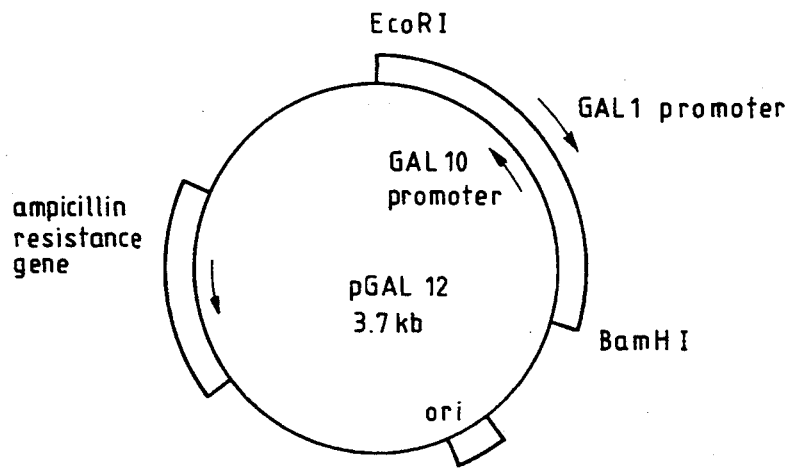

The peptide chain represented by $A_2$ is composed of 1–3 amino acids selected from the group consisting of Gly, Ala, Leu, Ile, Ser, Thr, Cys, Met, Asp, Asn, Glu, Gln, Lys, Arg, Phe, Tyr, His, Trp, Pro and Val. As the hydrophobic amino acids in the peptide chain X, there may be mentioned, for example, Leu, Phe, Ala, Ile, Val, Cys and Met. In a preferred embodiment, $A_1$ is -Arg-Ser-, $A_2$ is -Leu-Leu- and X is -(Leu)$_8$-.

A more preferred example of the signal peptide has the following amino acid sequence:

Met Arg Ser (Leu)$_{10}$ Pro Gly Cys Trp Ala

The signal peptide gene may have any DNA sequence which corresponds to the amino acid sequence mentioned hereinabove. For example, the following codons may be mentioned for the respective amino acids: GCT or GCC for Ala; TGT for Cys; GAC for Asp; GAA for Glu; TTC for Phe; GGT for Gly; GAC for His; ATT or ATC for Ile; AAG for Lys; TTG for Leu; ATG for Met; AAC for Asn; CCA for Pro; CCA for Gln; AGA for Arg; TCT or TCC for Ser; ACT or ACC for Thr; GTT or GTC for Val; TGG for Trp; TAC for Tyr. In a preferred embodiment, the following DNA sequence is employed:

| -18 | | | -15 | | | | | -10 | | |
|---|---|---|---|---|---|---|---|---|---|---|
| Met | Arg | Ser | Leu | Leu | Leu | Leu | Leu | Leu | Leu | Leu |
| ATG | AGA | TCT | TTG | TTG | TTG | TTG | TTG | TTG | TTG | TTG |

| | | -5 | | | | -1 |
|---|---|---|---|---|---|---|
| Leu | Leu | Pro | Gly | Cys | Trp | Ala |
| TTG | TTG | CCA | GGT | TGT | TGG | GCT |

The heterologous protein produced in accordance with the present invention is not limited to any particular species. Preferred examples are physiologically active substances such as human serum albumin, interferon-α, β or γ, urokinase, growth hormone, insulin and various lymphokines.

The genes coding for such heterologous proteins are described in JP-A-62-29985 or EP-A-206733 (human serum albumin), JP-A-61-185189 or DE-A-3603958 (interferon-α), JP-A-61-108397 or EP-A-190686 (interferon-γ), JP-A-60-180591 or EP-A-154272 (urokinase) and elsewhere (The term "JP-A" as used herein means an "unexamined published Japanese patent application").

In the above-cited references, plasmids containing the respective heterologous protein genes are disclosed.

The recombinant plasmid for yeast transformation as provided by the present invention may be prepared in a conventional manner as a plasmid containing the serum albumin signal peptide gene and a heterologous protein gene connected thereto downstream therefrom by per se known means.

The promoter and terminator are not limited to any particular species provided that they can function in yeast.

Suitable promoters are, for example, the PGK promoter [Nucleic Acid Res., 10(23), 7791 (1982)], ADH promoter (ibid.), phoE(5) promoter [J. Mol. Biol., 163(4), 513 (1983)], GAL1 promoter [Mol. Cell. Biol., 4(11), 2467 (1984)], GAL10 promoter (EP-A-132309), GAP-DH promoter [J. Biol. Chem., 258, 529 (1983)] and SUC2 promoter (EP-A-0127304).

The promoter is located upstream from the signal peptide gene.

Suitable for use as the terminator are the phoE(5) terminator [Cell, 12, 721–732 (1977)] and GAP-DH terminator [J. Biol. Chem., 254, 9839–9845 (1979)], among others.

The terminator is located downstream from the heterologous protein gene.

The promoter and terminator are available each in the form of a plasmid with the promoter and/or terminator inserted therein.

The plasmid DNA is not limited to any particular species provided that it is capable of autonomously replicating in a yeast. Specific examples are pJDB207 and pJDB219 (both commercially available from Amersham).

The recombinant plasmid according to the present invention can be prepared by excising a DNA sequence comprising the signal peptide gene-heterologous protein gene, a promoter-containing DNA sequence and a terminator-containing DNA sequence respectively from the above-mentioned plasmids by means of restriction enzymes, connecting (ligating) them together and inserting them into an appropriate plasmid or by excising a DNA sequence from one plasmid and inserting it into another plasmid.

In both case, the sequencing order should be adjusted as follow: from upstream to downstream, promoter-signal peptide gene-heterologous protein gene-terminator.

It is also possible to incorporate, as a selection marker, an antibiotic (tetracycline, ampicillin, kanamycin) resistance gene or a gene for complementing the auxotrophy of the host.

Suitable methods for transformant preparation using the DNA sequence according to the present invention include, for example, the method which comprises using a recombinant plasmid with said DNA sequence inserted therein and the method which comprises inserting said DNA sequence into the host (yeast) onto the chromosome thereof.

The preparation of a transformant using the recombinant plasmid and the production of the corresponding heterologous protein are performed in the following manner.

The recombinant plasmid is introduced into a host. Yeast cells are used as the host cells. More specifically, mutants with a mutation complementable by a selection marker gene borne by the plasmid to be inserted into the host, for example, the leucine-requiring mutant Saccharomyces cerevisiae AH22 (a, his 4, leu 2, can 1), are preferably used.

The transformation of host (yeast) cells is performed by a known method, for example the calcium phosphate precipitation method, protoplast polyethylene glycol fusion method or the electroporation method.

Necessary transformants are selected.

The transformant strain is cultivated in a known medium suitable for the host cells. As the medium, there may be mentioned, for example, YNB liquid medium [0.7% Yeast Nitrogen Base (Difco), 2% glucose] and YPD liquid medium [1% yeast extract (Difco), 2% polypeptone (Daigo Nutritive Chemicals), 2% glucose].

The cultivation is conducted generally at a temperature of from about 15° to 43° C. (preferably about 30° C.) for a period of from about 20 to 100 hours, if necessary with aeration and/or agitation.

After cultivation, the culture supernatant is recovered and the heterologous protein is purified by a per se known method, for example, by affinity chromatography, fractionation, ion exchange chromatography, gel filtration, concentration by ultrafiltration and so forth.

The method according to the present invention can produce desired heterologous proteins in the manner of secretory expression and, as compared with systems involving intracellular accumulation, can be expected to produce heterologous proteins more close in function and structure to natural proteins.

Whereas, in systems in which desired proteins are accumulated intracellularly, cell disruption and purification of the desired proteins from the disruption mixtures are required for recovery of the desired proteins. The method according to the present invention does not require such purification.

In particular, the selection of the signal peptide according to the invention as the signal peptide essential for secretory protein expression has led to the establishment of novel expression systems, which are thought to be of use for efficient expression of heterologous proteins.

The following examples are further illustrative of the invention but are by no means limitative of the scope thereof.

The techniques, reactions and analytical methods for use in the practice of the present invention are well known in the art. Unless otherwise indicated, all enzymes used are available from commercial sources, such as Takara Shuzo, New England Biolabs (NEB) (Massachusetts, U.S.A.), Amersham (Great Britain) and Bethesda Research Laboratories (BRL) (Maryland, U.S.A.).

Unless otherwise specified, buffers and reaction conditions for enzymatic reactions were used according to recommendations given by respective enzyme manufactures.

The transformation of *Escherichia coli* with plasmids, colony hybridization, electrophoresis and DNA recovery from gels were performed by the respective methods described in "Molecular Cloning" (Cold Spring Harbor Laboratory, 1981). The transformation of yeast was carried out by the method described in "Methods in Yeast Genetics" (Cold Spring Harbor Laboratory, 1981).

In the following example, the term "overnight" means "about 15 hours" and the term "room temperature" means "from about 15° to 25° C.

EXAMPLE

1. Cloning of yeast GAL1 and GAL10 promoters 1-1. Construction of yeast chromosomal DNA library The chromosomal DNA of the yeast strain *Saccharomyces cerevisiae* GRF18 PHO80 cir⁰ (EP-A-180958) was extracted and purified by the method of R. Cryer et al. [R. Cryer et al. (1974), Methods in Enzymol., 12, 39].

According to M. Johnson and R. W. Davis [M. Johnson and R. W. Davis (1984), Mol. Cell. Biol., 4, 1440-1448], the yeast GAL1, 10 promoter region resides on the yeast chromosome and digestion with the restriction enzymes EcoRI and XbaI gives said promoter as a DNA fragment of about 1 kb. Therefore, the yeast chromosome DNA extracted and purified as described in the above-cited reference was digested with EcoRI and XbaI and a DNA fragment of about of about 1 kb was isolated by electrophoresis. A plasmid, pUC19 (BRL), was digested with EcoRI and XbaI and dephosphorylated at the 5' end by treatment with calf intestine-derived alkaline phosphatase (CIP), the resultant cleaved plasmid was mixed with the above DNA fragment, and ligation was performed using a ligation kit (Takara Shuzo). The ligation product was introduced into competent cells of *Escherichia coli* JM109 (Takara Shuzo). YT agar plates containing 0.004% X-gal (5-bromo-4-chloro-3-indolyl-β-thiogalactopyranoside) and 1 mM IPTG (isopropyl-β-D-thiogalactopyranoside) (prepared by dissolving 8 g of polypeptone, 5 g of yeast extract and 5 g of sodium chloride in water to make 1 liter, adding 12 g of agar powder, sterilizing the solution by autoclaving, to the solution after it cooled, adding X-gal being dissolved in dimethylformamide, IPTG previously being dissolved in water followed by filter sterilization and ampicillin previously being dissolved in water followed by filter sterilization so as to give a final concentration of 40 μg/ml, distributing the solution into plastic dishes and allowing it to solidify) were smeared with the transformants and incubated overnight at 37° C. White colonies and blue colonies appeared. The DNA insert-containing white colonies alone were inoculated into L agar plates containing 40 μg/ml of ampicillin (prepared by dissolving 0.62 g of Tris base, 10 g of polypeptone, 5 g of yeast extract and 5 g of sodium chloride in water to make 1 liter, adding 12 g of agar powder, sterilizing the solution by autoclaving, to the solution after it cooled, adding ampicillin previously being dissolved in water followed by filter sterilization so as to give a final concentration of 40 μg/ml, distributing the solution into plastic dishes and allowing it to solidify) by means of a sterilized toothpick. The inoculum size was 100 colonies per plate. The agar plates were incubated overnight at 37° C. In this way, a library comprising about 5,000 colonies was prepared. The colonies formed were transferred to nitrocellulose filters, and the filters were immersed in a solution containing 0.5M sodium hydroxide and 1.5M sodium chloride for DNA denaturation and then neutralized with a solution containing 1.5M sodium chloride and 0.5M Tris-HCl, pH 7.5. *Escherichia coli* cell residues were removed by washing with 2×SSC (0.3M sodium chloride-0.03M sodium citrate, pH 7.0) and the filters were then air-dried and further dried under reduced pressure at 80° C. for 2 hours.

1-2. Probe preparation

A part of the base sequence of the gene coding for the GAL1, 10 promoter was synthesized by the phosphoamidite method using an Applied Biosystems model 381A DNA synthesizer. Its sequence is shown below.

5'-CTCTATACTTTAACGTCAAG-3'

This was purified by electrophoresis on a 7M urea-20% polyacrylamide gel. The purified DNA sequence was radiolabeled at the 5 ' end using [γ-$^{32}$P]ATP and T4 polynucleotide kinase. Thus, the reaction using 10 picomoles of the synthetic DNA, 250 μCi of [γ-$^{32}$P]ATP and 8 units of T4 polynucleotide kinase gave 2×10$^7$ cpm (Cherenkov counter) of the terminally $^{32}$P-labeled synthetic DNA probe. The synthetic DNA probe was purified by using NENSORB 20 (Du pont).

1-3. Screening for GAL1 and GAL10 promoters

Sets of 10 nitrocellulose filters with DNA immobilized thereon as obtained in the step 1-1 mentioned above were respectively placed in plastic bags and treated in the following manner. A prehybridization solution (10 ml) composed of 6×SSC, 0.1% sodium dodecyl sulfate (SDS) and 20 μg/ml of salmon sperm DNA heated at 100° C. for 5 minutes and then cooled on ice was added to each plastic bag, the bag was sealed and incubation was carried out at 40° C. for 3 hours. The prehybridization solution was discarded, 10 ml of a hybridization solution was added instead, and incubation was conducted overnight at 40° C. The hybridization solution had the following composition: 6×SSC, 0.1% SDS, 100 μg/mol salmon sperm DNA, and 7.5×10$^5$ cpm/ml $^{32}$P-probe. After incubation, each filter was transferred to a beaker and washed with 6×SSC, 0.1% SDS at 50° C. for 30 minutes, with 2×SSC, 0.1% SDS at 50° C. for 30 minutes, with 2×SSC, 0.1% SDS at 50° C. for 30 minutes, and finally with 0.1×SSC, 0.1% SDS at 50° C. for 30 minutes, in that order. The filters thus washed were air-dried, 100-200 cpm marks were spotted, and autoradiography was performed. As a result, two positive clones were obtained. One of the clones was shake-cultured overnight at 37° C. in Super broth containing 40 μg/ml of ampcillin [prepared by dissolving 12 g of Bacto-tryptone, 24 g of yeast extract and 5 ml of glycerol in water to make 900 ml and sterilizing the solution by autoclaving (solution A), separately dissolving 3.81 g of potassium dihydrogen phosphate and 12.5 g of dipotassium monohydrogen phosphate in water to make 100 ml and sterilizing the solution by autoclaivng (solution B), and mixing the solutions A and B in a ratio of 9:1 (v/v)]. Thereafter, the plasmid DNA was extracted and purified by the alkali-SDS method. The partial base sequence of this plasmid DNA (pGAL11, FIG. 1) as determined by the dideoxy method was in agreement with the sequence already reported [M. Johnston and R. W. Davis (1984), Mol. Cell. Biol., 4, 1440-1448]. pGAL11 contains the GAL1 promoter in the direction from the EcoRI site to the XbaI site and the GAL10 promoter in the reverse direction.

1-4. Conversion of XbaI site in pGAL11 to BamHI site

Since the human serum albumin gene has an XbaI site, the XbaI site in pGAL11 is unfavorable for ligation of the promoter sequence on pGAL11 with the signal peptide and the DNA sequence coding for the human serum albumin protein. Therefore, the XbaI site was converted to a BamHI site. Thus, pGAL11 was digested with XbaI, and the cohesive ends were filled in using *Escherichia coli*-derived DNA polymerase I Klenow fragment in the presence of dGTP, dATP, dTTP and dCTP. To this DNA fragment was added the 5'-terminally phosphorylated BamHI linker pCGGATCCG and ligated with said DNA fragment in the presence of T4 DNA ligase. The ligation product was digested with BamHI and again ligated in the presence of T4 DNA ligase, and the ligation product was introduced into *Escherichia coli* HB101 (EP-A-13828). From among the transformants obtained, a plasmid (pGAL12)-carrying clone was obtained. The GAL1 and GAL10 promoters can be isolated as a DNA fragment of about 1 kb by digestion of pGAL12 with EcoRI and BamHI.

Figure 2:
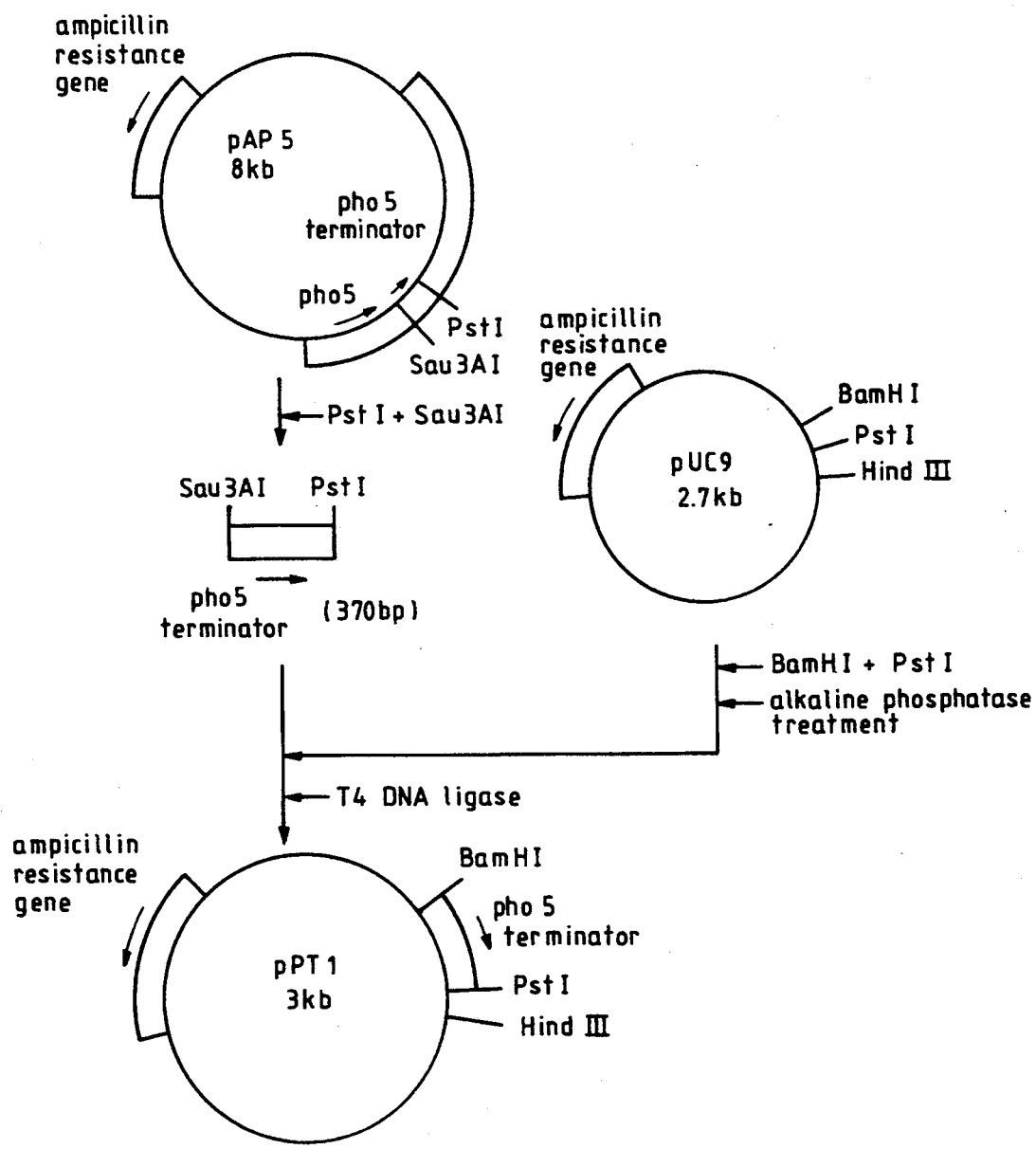
FIG. 2 shows a process for constructing a plasmid, pPT1, containing the pho5 terminator alone from a plasmid, pAP5, containing the whole pho5 gene and a plasmid, pUC9.

2. Construction of *Escherichia coli*-yeast shuttle vector, pPT2, containing yeast pho5 terminator The plasmid pAP5 with the *Saccharomyces cerevisiae* pho5 gene cloned therein as described in JP-A-62-151183 or EP-A-216573 was digested with the restriction enzymes Sau3AI and PstI, and a DNA fragment of about 370 bp with the pho5 terminator cloned therein was isolated by electrophoresis (FIG. 2). The commercially available plasmid pUC9 was digested with BamHI and PstI and, after alkaline phosphatase treatment, the digest was ligated with the above-mentioned 370-bp fragment. The base sequence of the Sau3AI cleavage site of the 370-bp fragment is

```
           GATCC ...
               G ...
``` and, when this is ligated with the BamHI cohesive end, a BamHI site is regenerated. Therefore, the plasmid obtained by the above ligation reaction (pPT1), when digested with BamHI and PstI or with BamHI and HindIII, gives the pho5 terminator-containing 370-bp DNA fragment (FIG. 2).

Figure 3:
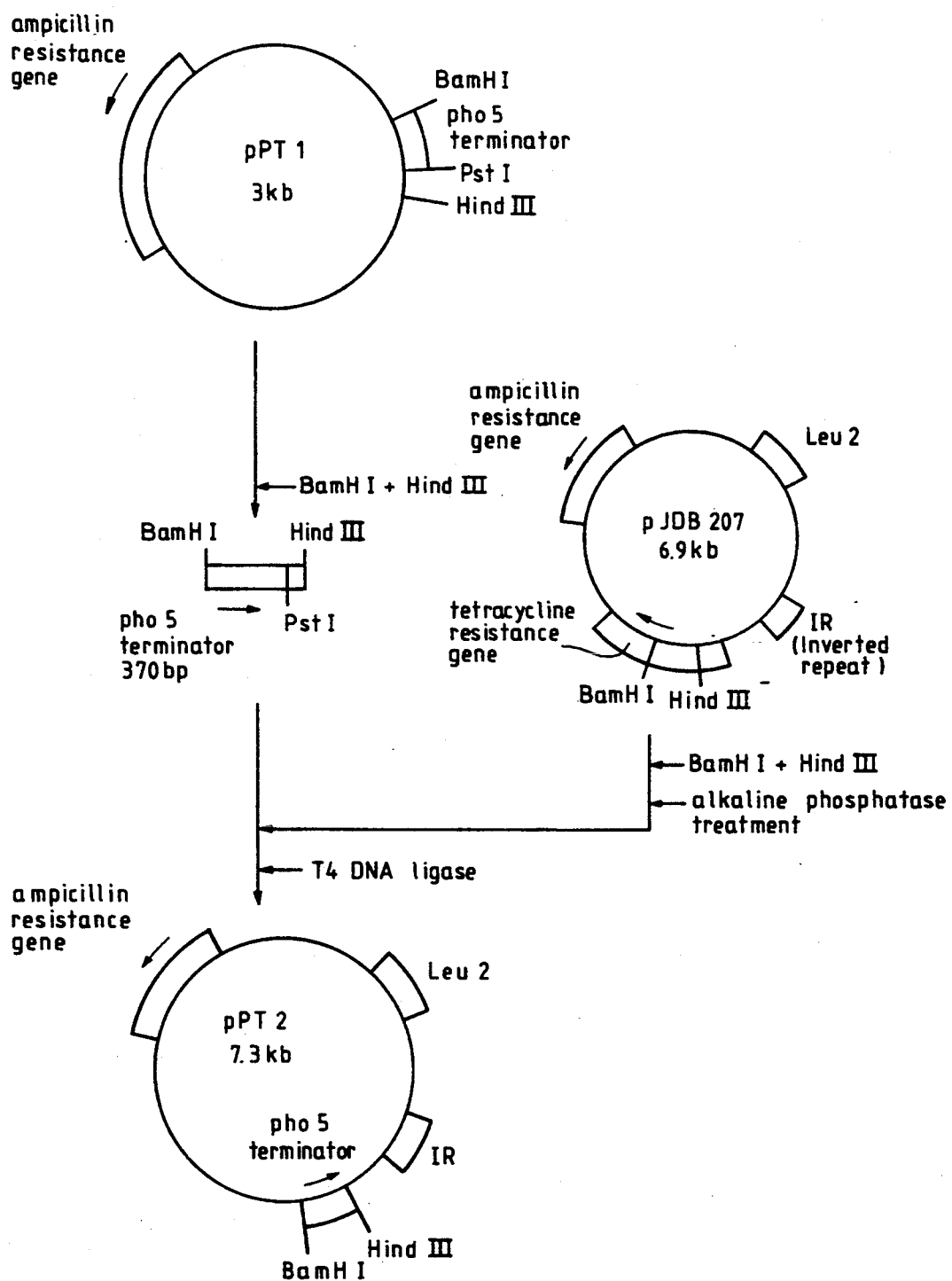
FIG. 3 shows a process for constructing a plasmid, pPT2, from the pho5 terminator-containing plasmid pPT1 and a plasmid, pJDB207.

The commercially available shuttle vector pJDB207 (FIG. 3) is capable of autonomously replicating in *Escherichia coli* and yeast. This shuttle vector was digested with BamHI and HindIII and then treated with alkaline phosphatase. pPT1 was digested with BamHI and HindIII, and a pho5 terminator-containing DNA fragment of about 370 bp was isolated by electrophoresis and ligated with the above-mentioned pJDB207. From among the transformants obtained with the ligation product, a clone carrying the plasmid pPT2 shown in FIG. 3 was obtained. pPT2 is an *Escherichia coli*-yeast shuttle vector containing the pho5 terminator and has a β-lactamase-due ampicillin resistance marker in *Escherichia coli* and a leucine requirement-complementing marker in yeast.

3. Human serum albumin gene

Figure 4:
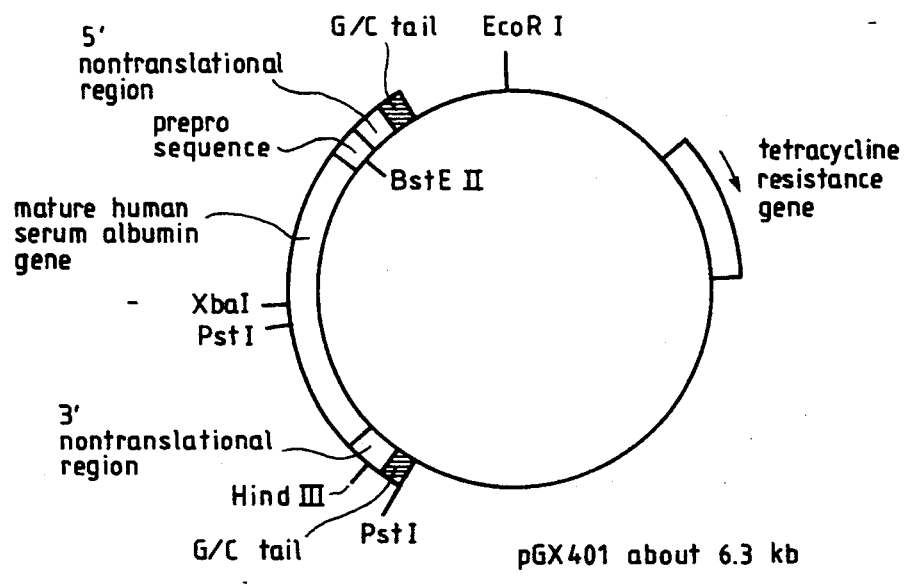
FIGS. 4 and 5 show the restriction enzyme map of a prepro-human serum albumin gene-containing plasmid, pGX401.
Figure 5:
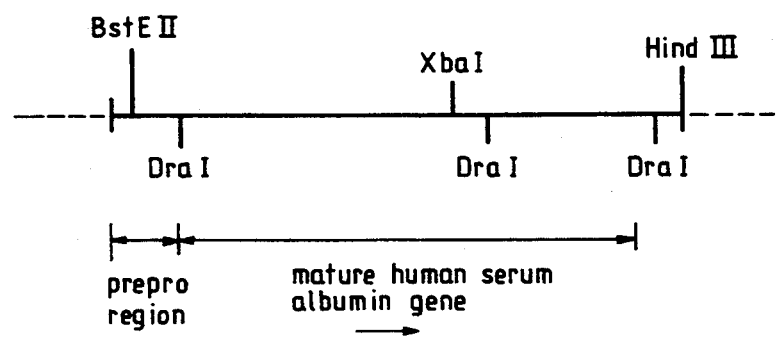
Figure 6:
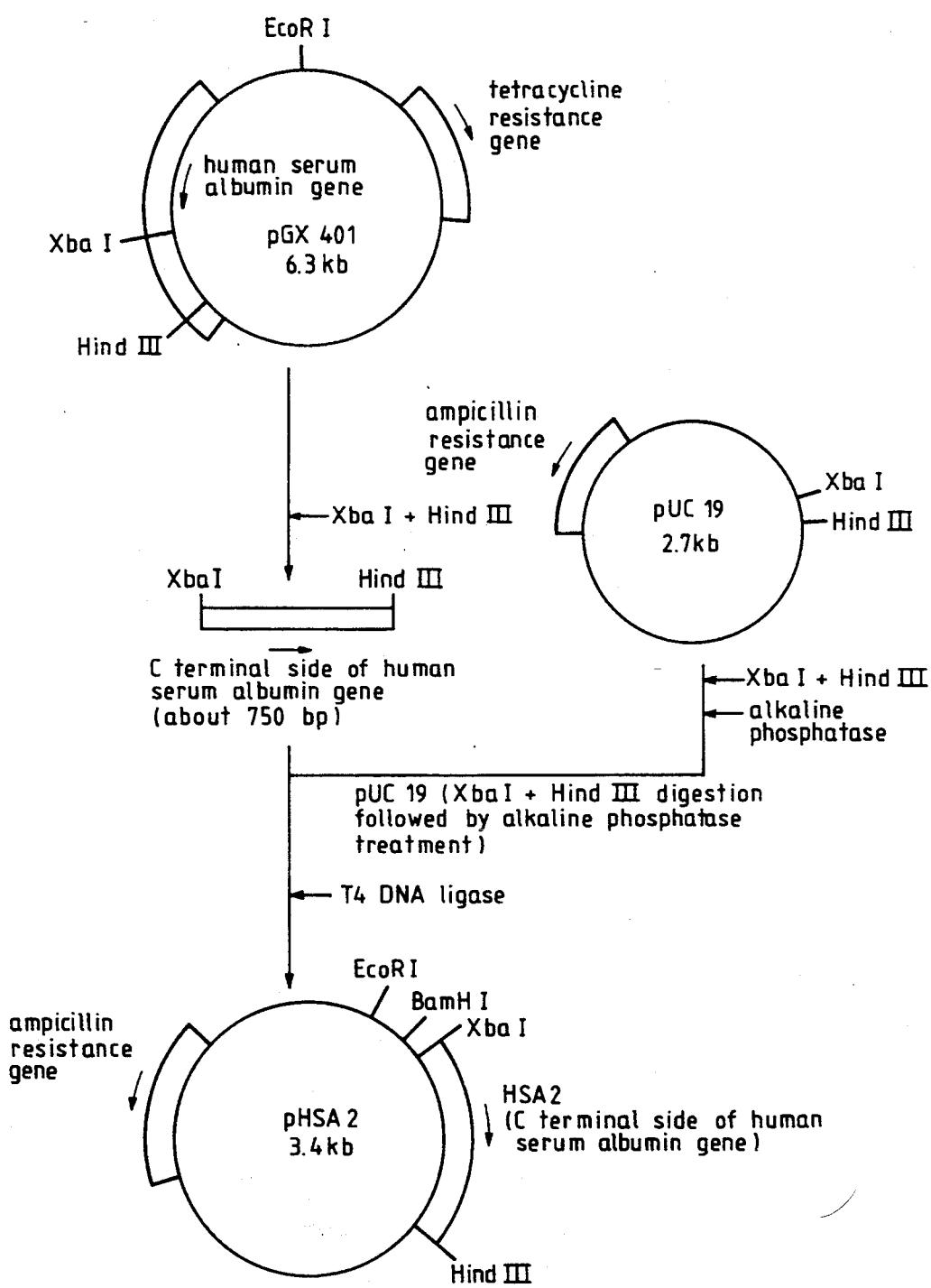
FIG. 6 shows a process for constructing a plasmid, pHSA2, containing the C-terminal side of the human serum albumin gene from the plasmid pGX401 and a plasmid, pUC19.

A DNA sequence coding for human serum albumin was derived from the prepro-human serum albumin gene-containing plasmid, pGX401 (FIG. 4, FIG. 5) described in JP-A-62-29985 or EP-A-206733 in the following manner. The plasmid pGX401 was digested with the restriction enzymes XbaI and HindIII, and a DNA fragment (HSA2) (about 750 bp) coding for C-terminal side amino acid sequence $^{357}$Leu-$^{585}$Leu of the human serum albumin protein and the 3' nontranslational region was isolated by electrophoresis. The commercially available plasmid pUC9 was digested with XbaI and HindIII, then further treated with alkaline phosphatase fox dephosphorylation at the 5' end and ligation with HSA2 in the presence of T4 DNA ligase. The ligation mixture was used to transform *Escherichia coli* HB101. From among the transformants obtained, a clone carrying the plasmid pHSA2 shown in FIG. 6 could be isolated. pGX401 was digested with DraI and XbaI, and a DNA fragment of about 1 kb was isolated by electrophoresis. This DNA fragment is a DNA sequence coding for the N-terminal side amino acid sequence $^{12}$Lys-$^{354}$Thr of the human serum albumin protein.

The DNA sequence shown below, which codes for the N-terminal amino acid sequence $^{1}$Asp-$^{11}$Phe of the mature human serum albumin protein, was synthesized by the phosphoamidite method using an Applied Biosystems model 381A DNA synthesizer.

|   | 1<br>Asp | 2<br>Ala | 3<br>His | 4<br>Lys | 5<br>Ser | 6<br>Glu | 7<br>Val | 8<br>Ala | 9<br>His | 10<br>Arg | 11<br>Phe |
|---|---|---|---|---|---|---|---|---|---|---|---|
| c | GAC | GCA | CAC | AAG | AGT | GAG | GTT | GCT | CAT | CGG | TTT |
| G | CGT | GTG | TTC | TCA | CTC | CAA | CGA | GTA | GCC | AAA |  |

While the codon coding for aspartic acid (Asp) was GAT in pGX401, the codon GAC was used here. As a result, ligation of the above synthetic DNA with the above-mentioned pGX401-derived DNA fragment of about 1 kb and insertion of the ligation product into pUC19 at the SalI-XbaI site result in SalI site regeneration. Furthermore, digestion with HincII gives a DNA sequence coding for an amino acid sequence beginning with the N-termial $^{1}$Asp of mature human serum albumin.

Figure 7:
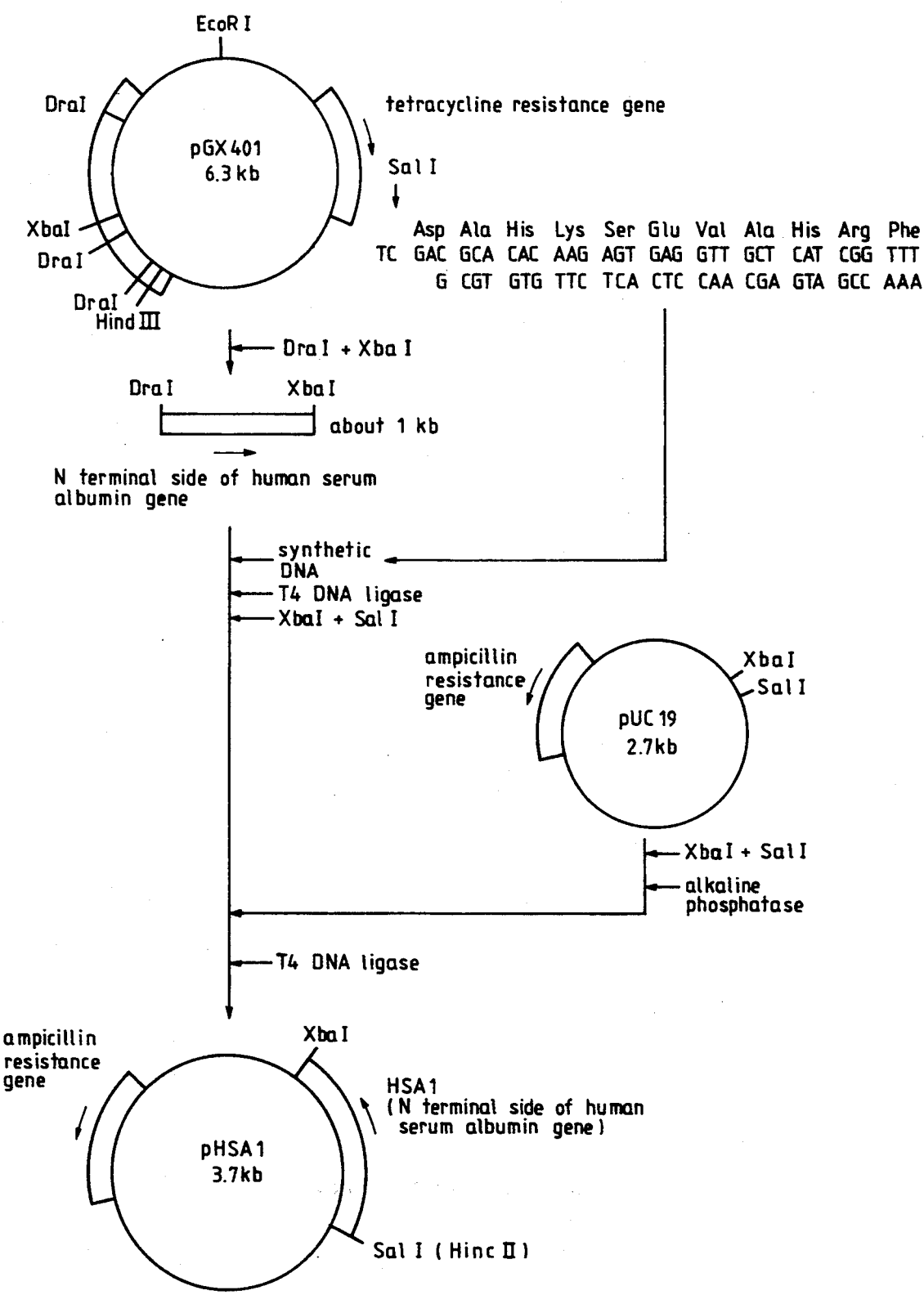
FIG. 7 shows a process for constructing a plasmid, pHSA1, containing the N-terminal side of the human serum albumin gene from the plasmids pGX401 and pUC19.

The above synthetic DNA was phosphorylated at the 5' end with ATP and T4 polynucleotide kinase and ligated in the presence of T4 DNA ligase with HSA1 isolated from DraI and XbaI digest of pGX401 by electrophoresis. The ligation mixture was used to transform *Escherichia coli* HB101 and, from among the transformants obtained, a clone carrying the plasmid pHSA1 shown in FIG. 7 was obtained.

4. Construction of plasmid DNA for secretory expression of human serum albumin by yeast A DNA sequence coding for a recombinant pre-human serum albumin protein resulting from connection of the signal peptide shown below, which is an example of the universal signal peptide represented by the amino acid sequence (I), to the N terminus of the mature human serum albumin protein was constructed as a plasmid capable of secretory expression in *Saccharomyces cerevisiae*. The universal signal peptide has the amino acid sequence Met Arg Ser Leu Leu Leu Leu Leu Leu Leu Leu
    Leu Leu Pro Gly Cys Trp Ala and falls within the scope of the amino acid sequence (I).

A DNA sequence coding for the amino acid sequence of the above-mentioned signal peptide was synthesized by the phosphoamidite method using an Applied Biosystems model 381A DNA synthesizer. The DNA sequence in shown below.

|  | −18<br>Met | | −15<br>Ser | Leu | Leu | Leu | Leu | Leu | −10<br>Leu |
|---|---|---|---|---|---|---|---|---|---|
|  |  | Arg |  |  |  |  |  |  |  |
| GATCC | ATG | AGA | TCT | TTG | TTG | TTG | TTG | TTG | TTG |
| G | TAC | TCT | AGA | AAC | AAC | AAC | AAC | AAC | AAC |

|  |  |  |  | −5 |  |  |  | −1 |
|---|---|---|---|---|---|---|---|---|
| Leu | Leu | Leu | Leu | Pro | Gly | Cys | Trp | Ala |
| TTG | TTG | TTG | TTG | CCA | GGT | TGT | TGG | GCT |
| AAC | AAC | AAC | AAC | GGT | CCA | ACA | ACC | CGA |

Figure 8:
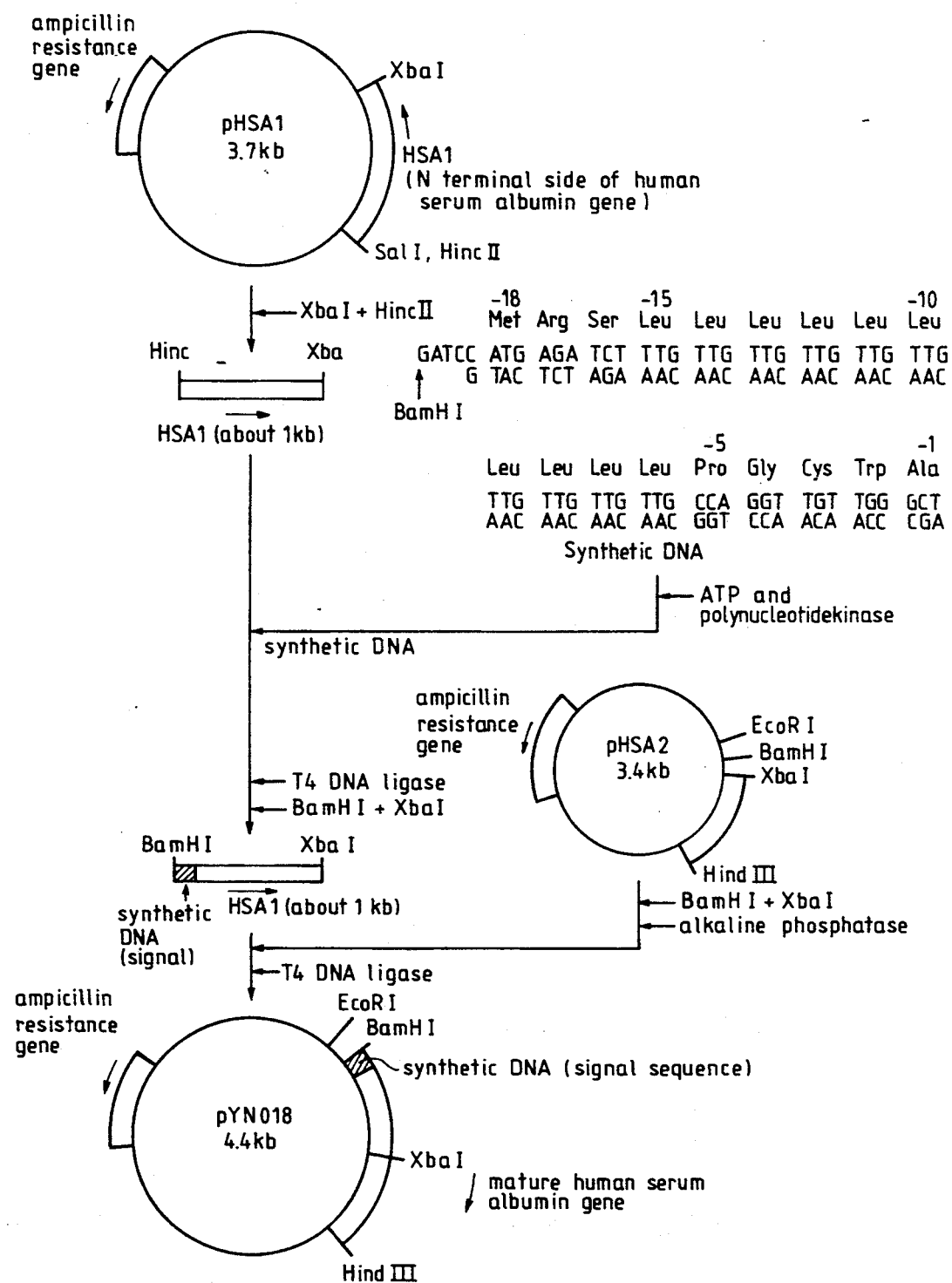
FIG. 8 shows a process for constructing a signal peptide gene- and mature human serum albumin gene-containing plasmid, pYNO18, from pHSA1, pHSA2 and a synthetic signal peptide gene.
Figure 9:
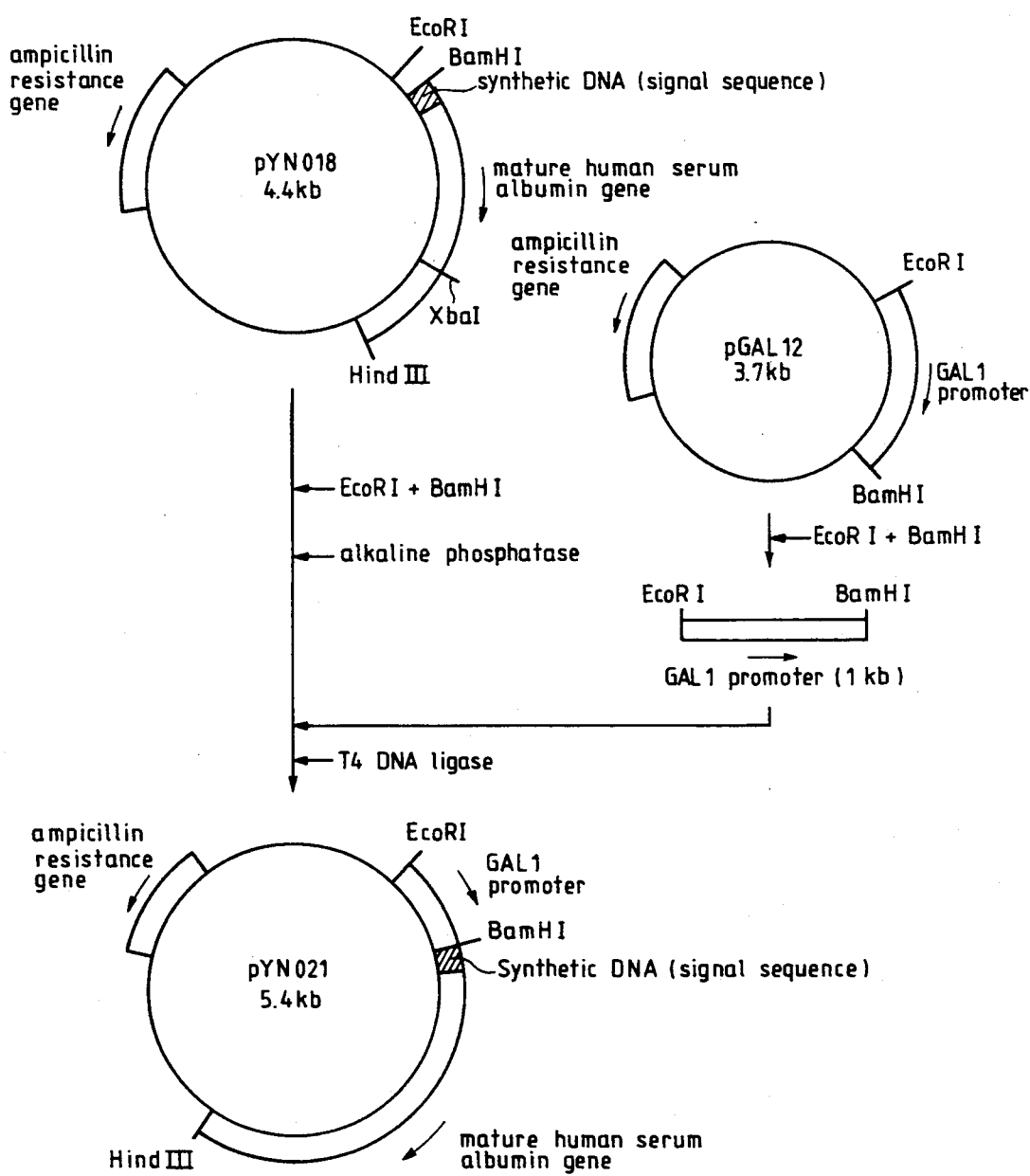
FIG. 9 shows a process for constructing a GAL 1 promoter-, signal peptide gene- and mature human serum albumin gene-containing plasmid, pYNO21, from the plasmids pYNO18 and pGAL12.
Figure 10:
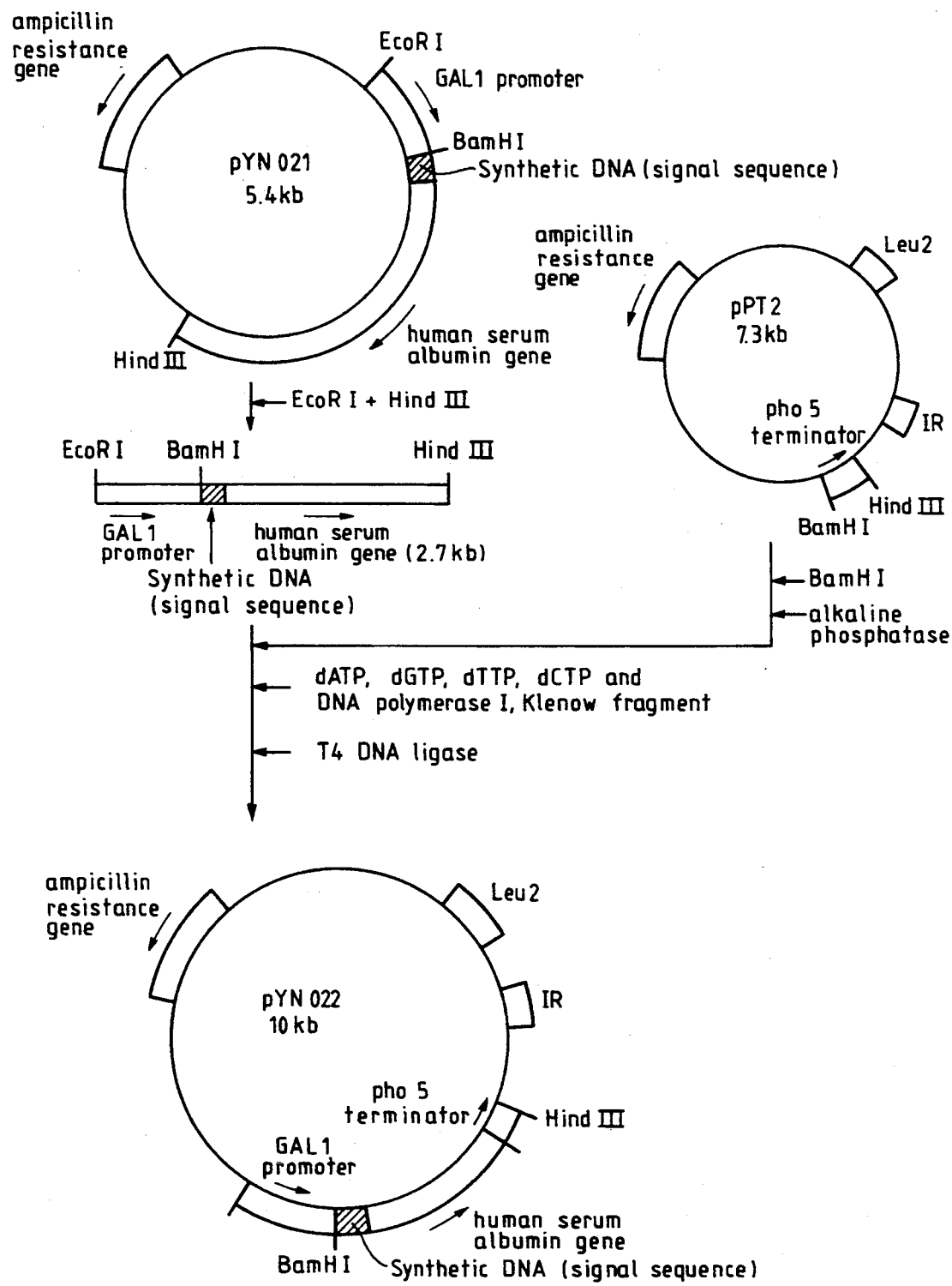
FIG. 10 shows a process for constructing a GAL1 promoter-, signal peptide gene-, mature human serum albumin gene- and pho5 terminator-containing plasmid, pYNO22, from the plasmids pYNO21 and pPT2.

The above synthetic DNA was phosphorylated at the 5' end with ATP and T4 polynucleotide kinase. Separately, pHSA1 was digested with XbaI and HincII, and the DNA sequence HSA1 (about 1 kb) coding for the N-terminal side of the human serum albumin protein was isolated by electrophoresis. The above phosphorylated synthetic DNA and HSA1 were mixed together and ligated together using T4 DNA ligase, and the ligation product was further digested with XbaI and BamHI. pHSA2 was digested with XbaI and BamHI and then treated with alkaline phosphatase. These DNAs were mixed together and ligated together in the presence of T4 DNA ligase, and the ligation mixture was used to transform competent cells of Escherichia coli HB101. From among the transformants obtained, a clone carrying the plasmid pYNO18 shown in FIG. 8 was obtained.

pYNO18 was digested with EcoRI and BamHI and then treated with alkaline phosphatase. pGAL12 was digested with EcoRI and BamHI, and a GAL1 promoter-containing DNA fragment of about 1 kb was isolated by electrophoresis and mixed with the pYNO18 treated in the above manner and ligated with the same in the presence of T4 DNA ligase. From among the tranformants obtained, a clone carrying the plasmid pYNO21 shown in FIG. 9 was obtained. pYNO21 is a plasmid DNA resulting from insertion at the EcoRI-HindIII site of pUC19 of the GAL1 promoter, the consensus signal peptide-encoding DNA sequence located downstream from the GAL1 promoter, the mature human serum albumin protein-encoding DNA sequence located directly after the signal peptide-encoding DNA sequence, and the human serum albumin cDNA-derived 3' nontranslational region directly following the mature protein-encoding DNA sequence, in that order.

pYNO21 was digested with EcoRI and HindIII, and a DNA fragment (2.7 kb) coding for the GAL1 promoter, signal peptide, mature human serum albumin protein and nontranslational region was isolated by electrophoresis. Separately, pPT2 was digested with BamHI and further treated with alkaline phosphatase. This was mixed with the above-mentioned 2.7-kb DNA fragment and the cohesive ends were filled in with DNA polymerase I Klenow fragment in the presence of dATP, dGTP, dTTP and dCTP. Furthermore, ligation was performed with T4 DNA ligase and the ligation mixture was used to transform Escherichia coli HB101. From among the transformants obtained, a clone carrying the plasmid pYNO22 shown in FIG. 10 was obtained. pYNO22 is a plasmid capable of autonomously replicating in Escherichia coli and in yeast and has, under the control of the GAL1 promoter capable of functioning in yeast, a DNA sequence coding for the consensus signal peptide mature human serum albumin protein in succession. Furthermore, pYNO22 has an ampicillin resistance gene to be expressed in Escherichia coli and a leucine requirement-complementation gene to be expressed in yeast. These genes can be used as markers in transformant selection.

5. Introduction of pYNO22 plasmid into yeast and secretory expression of human serum albumin The plasmid pYNO22 for secretory expression of human serum albumin was introduced into Saccharomyces cerevisiae AH22 in the following manner.

Saccharomyces cerevisiae AH22 was shake-cultured in 50 ml of YPD medium (prepared by dissolving 10 g of yeast extract and 20 g of Bacto-peptone in water to make 900 ml, sterilizing the solution by autoclaving and mixing the solution with 100 ml of 20% glucose solution separately sterilized by autoclaving) overnight at 37° C. Cells were collected by centrifugation, suspended in 20 ml of water and again collected by centrifugation. The cells thus obtained were suspended in 10 ml of a solution containing 50 mM dithiothreitol, 1.2M sorbitol and 25 mM EDTA, pH 8.5, and the suspension was shaken gently at 30° C. for 10 minutes. Cells were collected by centrifugation, suspended in 10 ml of 1.2M sorbitol, and again collected by centrifugation. The cells collected were suspended in 10 ml of 1.2M sorbitol and collected by centrifugation. The cells were suspended in 10 ml of a solution containing 0.2 mg/ml zymolyase 100T, 1.2M sorbitol, 10 mM EDTA and 0.1M sodium citrate, pH 5.8, and the suspension was shaken gently at 30° C. for 1 hour. Cells were collected by centrifugation, washed with 10 ml of 1.2M sorbitol, 10 ml of 10 mM calcium chloride and 10 ml of 1.2M sorbitol in that order, and cells were collected by centrifugation. The cells were suspended in 1 ml of a solution containing 10 mM calcium chloride and 1.2M sorbitol. A 100-$\mu$l portion of the suspension was placed in a sterilized test tube, 5 $\mu$l (5 $\mu$g) of pYNO22 was admixed with the suspension, and the mixture was allowed to stand at room temperature for 15 minutes. Further, 1.2 ml of a solution containing 20% polyethylenglycol 4000, 10 mM calcium chloride and 10 mM Tris-HCl, pH 7.5, was added and, after gentle shaking for mixing, the mixture was allowed to stand at room temperature for 20 minutes. Cells were collected by centrifugation and suspended in 0.1 ml of YPD medium containing 1.2M sorbitol and 10 mM calcium chloride, and the suspension was shaken gently at 30° C. for 30 minutes. A 1-$\mu$l, 5-$\mu$l, 10-$\mu$l, 20-$\mu$l or 50-$\mu$l portion of the suspension was added to 10 ml of a solution containing 1.2M sorbitol, 3% noble agar, 2% glucose and 0.7% yeast nitrogen base, and each suspension was spread on a plate composed of 1.2M sorbitol, 3% Bacto-agar, 2% glucose and 0.7% yeast nitrogen base. After solidification of the plate, incubation was performed at 30° C. for 3 days. The colonies formed were collected by means of a toothpick, suspended in 3 ml of a solution containing 0.7% yeast nitrogen base and 2% glucose, and shake-cultured at 30° C. for 2 days. A 1.5-ml portion of the culture broth was centrifuged, the cells thus collected were suspended in 3 ml of YPG medium (prepared by dissolving 10 g of yeast extract and 20 g of Bacto-peptone in water to make 900 ml, sterilizing the solution by autoclaving, and mixing the solution with 100 ml of 20% galactose separately sterilized by autoclaving), and the culture was incubated at 30° C. with shaking. The human serum albumin concentration of the culture supernatant was determined by the RPHA method. After 1 day, a maximum of 2 $\mu$g/ml of human serum albumin was detected; after 2 days, a maximum of 10 μg/ml; and after 3 days, a maximum of 40 μg/ml.

The human serum albumin secreted by the recombinant yeast into the medium was highly purified (purity: 95% or more) and examined for the N-terminal amino acid sequence. The sequence down to the 7th amino acid was found to be in agreement with the corresponding sequence of plasma-derived human serum albumin. Therefore, the recognition and cleavage by signal peptidase had taken place correctly.

While the invention has been described in detail and with reference to specific embodiments thereof, it will be apparent to one skilled in the art that various changes and modifications can be made therein without departing from the spirit and scope thereof.

What is claimed is:

1. An isolated DNA sequence coding for a signal peptide consisting of the amino acid sequence:

Met-$A_1$-$A_2$-X-B-C-D-E-F wherein $A_1$ is a peptide chain composed of 1–3 amino acids each selected from the group consisting of Arg, Ser, Lys and His, $A_2$ is a peptide chain composed of 1–3 amino acids selected from the group consisting of Gly, Ala, Leu, Ile, Ser, Thr, Cys, Met, Asp, Asn, Glu, Gln, Lys, Arg, Phe, Tyr, His, Trp, Pro and Val, X is a peptide chain composed of 8–10 hydrophobic amino acids, B is Pro or Ser, C is Gly or Pro, D is an amino acid selected from the group consisting of Cys, Ala, Leu, Ser, Thr and Val, E is Trp or Gln and F is Ala or Gly.

2. An expression vector comprising the DNA encoding a signal peptide of claim 1.

3. The expression vector of claim 2, wherein the DNA encoding a signal peptide is linked operably to a DNA encoding a heterologous protein.

4. The vector sequence of claim 3, wherein said heterologous protein is human serum albumin.

5. The expression vector of claim 3, further comprising a promoter capable of functioning in a yeast cell operably linked to said DNA encoding a signal peptide and a terminator capable of functioning in a yeast cell operably linked to said DNA encoding heterologous protein.

6. A recombinant plasmid capable of autonomously replicating in a yeast comprising the DNA sequence of claim 2.

7. A yeast transformed with the DNA sequence of claim 2.

8. A DNA sequence as claimed in claim 1, wherein $A_2$ is Leu-Leu-.

9. A DNA sequence as claimed in claim 1, wherein X is -(Leu)$_8$-.

10. A DNA sequence as claimed in claim 1, wherein $A_1$ is -Arg-Ser-, $A_2$ -Leu-Leu- and X is -(Leu)$_8$-.

11. A DNA sequence as claimed in claim 1, wherein Met-$A_1$-$A_2$-X-B-C-D-E-F is MetArgSer(Leu)$_{10}$ProGlyCysTrpAla.

12. The vector of claim 5, wherein said heterologous protein is human serum albumin.

13. The yeast of claim 7, wherein said vector is integrated in a chromosome of said yeast.

* * * * *